(12) United States Patent
Tchirikov

(10) Patent No.: US 9,295,457 B2
(45) Date of Patent: Mar. 29, 2016

(54) BALLOON CATHETER SYSTEM FOR SEALING PUNCTURE POINTS IN BODY CAVITIES, HOLLOW ORGANS OR IN PERCUTANEOUS SYSTEMS IN MAMMALS

(75) Inventor: Michael Tchirikov, Halle (DE)

(73) Assignee: Universitätsmedizin der Johannes Gutenberg Universität Mainz, Mainz (DE)

(*) Notice: Subject to any disclaimer, the term of this patent is extended or adjusted under 35 U.S.C. 154(b) by 478 days.

(21) Appl. No.: 13/696,461

(22) PCT Filed: Apr. 20, 2011

(86) PCT No.: PCT/EP2011/002006
§ 371 (c)(1),
(2), (4) Date: Jan. 3, 2013

(87) PCT Pub. No.: WO2011/137978
PCT Pub. Date: Nov. 10, 2011

(65) Prior Publication Data
US 2013/0096499 A1 Apr. 18, 2013

(30) Foreign Application Priority Data
May 6, 2010 (DE) .......................... 10 2010 019 795

(51) Int. Cl.
*A61M 29/00* (2006.01)
*A61B 17/00* (2006.01)
*A61B 17/42* (2006.01)
(Continued)

(52) U.S. Cl.
CPC .............. *A61B 17/0057* (2013.01); *A61B 17/42* (2013.01); *A61M 25/1011* (2013.01); *A61B 2017/00539* (2013.01); *A61B 2017/00557* (2013.01); *A61B 2017/22067* (2013.01)

(58) Field of Classification Search
CPC .......... A61M 25/104; A61M 25/1015; A61M 25/1011; A61M 17/42; A61M 17/0057; A61M 2017/22067; A61M 2017/00539
USPC ................................ 604/509, 101.01, 101.05
See application file for complete search history.

(56) References Cited

U.S. PATENT DOCUMENTS

| 2,799,273 A | 7/1957 | Oddo |
| 3,154,077 A | 10/1964 | Cannon |

(Continued)

FOREIGN PATENT DOCUMENTS

| EP | 0121571 | 10/1983 |
| EP | 2011002006 | 11/2011 |

(Continued)

*Primary Examiner* — Edelmira Bosques
(74) *Attorney, Agent, or Firm* — McHale & Slavin, P.A.

(57) ABSTRACT

The present invention relates to a balloon catheter system for sealing puncture points or openings in body cavities, hollow organs or in percutaneous drainage operations in mammals, consisting of a filling catheter on the distal end of which a first balloon can be filled with the filling medium is arranged with a further balloon arranged proximally spaced apart therefrom. The balloons close the puncture point or the opening on the two sides in the filled state of the balloon. A hollow needle open at the shaft or the shaft end can be guided in the lumen of the filling catheter for filling the two balloons with the filling medium, wherein the shells of the two balloons enclose the shaft of the filling catheter. The filling catheter in each case has an opening arranged in the balloon lumen to fill the two balloons.

13 Claims, 1 Drawing Sheet

(51) Int. Cl.
*A61M 25/10* (2013.01)
*A61B 17/22* (2006.01)

(56) References Cited

U.S. PATENT DOCUMENTS

| | | | |
|---|---|---|---|
| 3,509,884 A | 5/1970 | Bell | |
| 3,543,758 A | 12/1970 | McWhorter | |
| 4,100,923 A | 7/1978 | Southern | |
| 4,198,981 A | 4/1980 | Sinnreich | |
| 4,836,204 A | 6/1989 | Landymore et al. | |
| 4,946,449 A * | 8/1990 | Davis, Jr. | 604/256 |
| 5,104,377 A | 4/1992 | Levine | |
| 5,211,624 A | 5/1993 | Cinberg et al. | |
| 5,725,551 A * | 3/1998 | Myers | A61B 17/0057 604/285 |
| 6,623,452 B2 * | 9/2003 | Chien et al. | 604/103.01 |
| 6,893,430 B2 * | 5/2005 | Eshel et al. | 604/544 |
| 2005/0027247 A1 | 2/2005 | Carrison et al. | |
| 2008/0132937 A1 * | 6/2008 | Hartley et al. | 606/194 |
| 2009/0088788 A1 | 4/2009 | Mouw | |
| 2009/0187144 A1 * | 7/2009 | Jayaraman | 604/103.02 |
| 2009/0204099 A1 | 8/2009 | Feloney | |

FOREIGN PATENT DOCUMENTS

| | | |
|---|---|---|
| JP | 5431985 | 3/1979 |
| WO | WO2011137978 | 11/2011 |

* cited by examiner

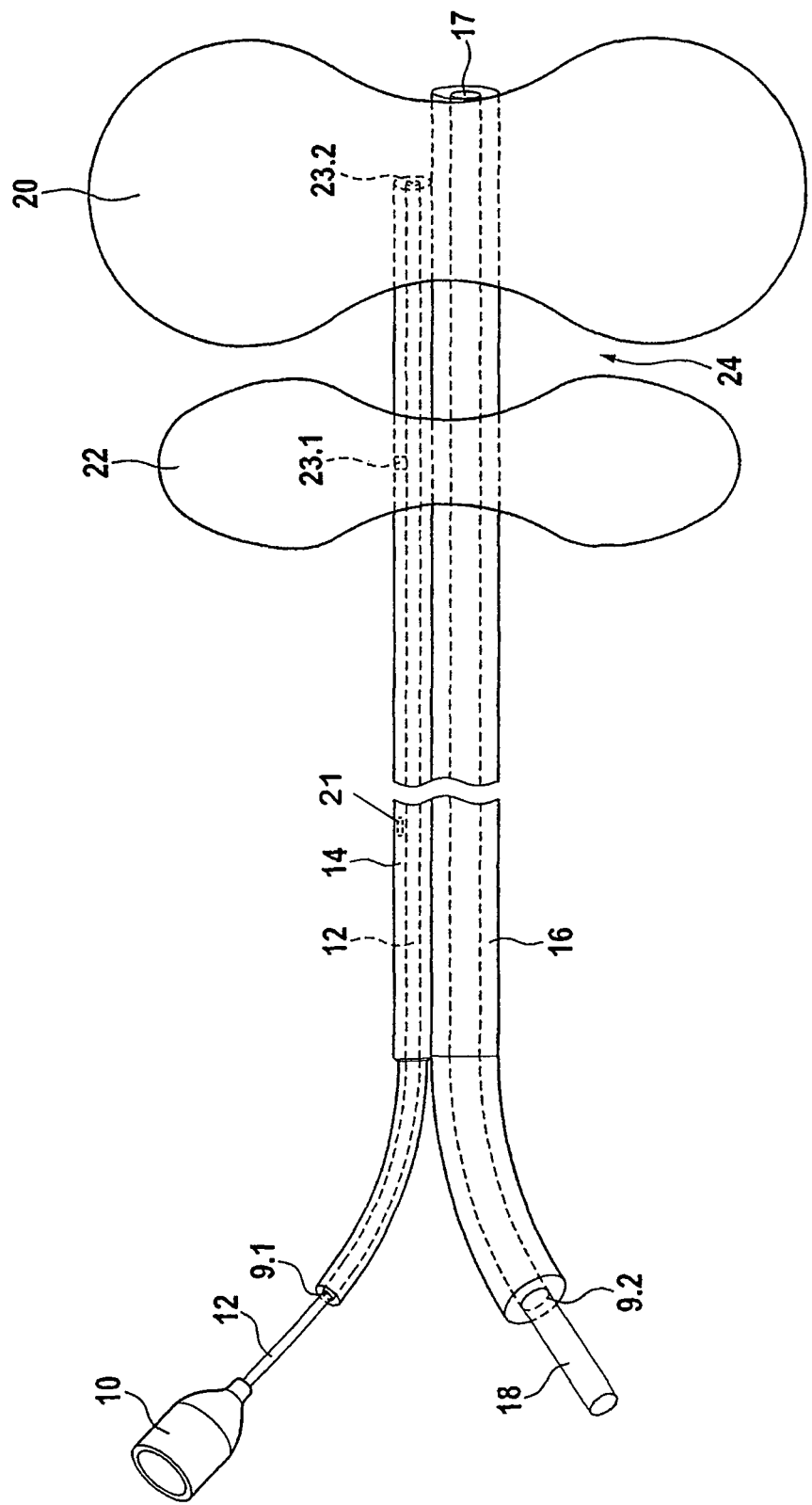

BALLOON CATHETER SYSTEM FOR SEALING PUNCTURE POINTS IN BODY CAVITIES, HOLLOW ORGANS OR IN PERCUTANEOUS SYSTEMS IN MAMMALS

CROSS REFERENCE TO RELATED APPLICATIONS

This is a national stage filing in accordance with 35 U.S.C. §371 of PCT/EP2011/002006, filed Apr. 20, 2011, which claims the benefit of the priority of German Patent Application No. 102010019795.5, filed May 6, 2010, the contents of each are incorporated herein by reference.

FIELD OF THE INVENTION

The present invention relates to a balloon catheter system for sealing puncture points in body cavities, hollow organs or in percutaneous systems in mammals. The catheter is suitable for treatment in a preterm premature rupture of the membranes (PPROM, PROM), a percutaneous gastrostoma and for percutaneous drainage. In particular, the invention relates to a balloon catheter for sealing puncture points or openings in body cavities, hollow organs or in percutaneous drainage operations in mammals. The balloon catheter system according to the invention is suitable for treating a preterm premature rupture of the membranes (PPROM) by amnioinfusion, a gastrointestinal anastomosis, a bowel obstruction (ileus), drainage of bile from the gallbladder, a pleural effusion, a pericardial effusion or a perianal abscess.

DESCRIPTION OF THE BACKGROUND ART

An early preterm premature rupture of membranes (PPROM) occurs in about 3 to 17% of all pregnancies and leads to a premature birth within a few days in most cases. PPROM is therefore the cause of child morbidity and mortality in the early weeks of pregnancy, in particular before the completed $34^{th}$ week of pregnancy. Ascending infections from the lower genital tract, which can lead to PPROM through the increase in the intraamnial pressure and the occurrence of shear forces, are one reason for the occurrence of a preterm premature rupture of the membranes.

Therapeutic measures for treating PPROM aim to restore and maintain the normal fluid volume in the amnion. To increase the amniotic fluid index (AFI), the volume of fluid of the amnion is continuously increased by means of an amnioinfusion (Tan L.-K et al., Test Amnioinfusion to Determine Suitability for Serail Therapeutic Amnioinfusion in Midtrimester Premature Rupture of Membranes, Fetal Diagn Ther (2003), 18: 183-189; Luigi A. et al., Transabdominal amnioinfusion in preterm premature rupture of membranes: a randomised controlled trial, BJOG: an International Journal of Obstetrics and Gynaecology (2005), Vol. 112, pp. 759-763; Tian-Lun Hsu et al., The Experience of Amnioinfusion for Oligohydramnios during the early second trimester, Taiwan J Obstet Gynacol (2007), Vol. 46 (4)).

The previously known methods for amnioinfusion for treating PROM are unsatisfactory, as the artificial amniotic fluid introduced from outside (physiological saline solution) very rapidly flows out of the uterus again, so the effect of the amnioinfusion is greatly reduced. The known methods related, for example, to a cervical occlusion with a fibrin gel (Zamlynski J, Bodzek P, Olejek A, Grettka K, Manka G., Results of amnioinfusion in pregnancies with oligohydramnios and non-ruptured fetal membranes, Med Wieku Rozwoj 2003; 7: 187-94) or the infusion of a fluid by means of a transcervical catheter (Machalski T, Sikora J, Bakon I, Magnucki J, Grzesiak-Kubica E, Szkodny E. Short-term and long-term fetal heart rate variability after amnioinfusion treatment of oligohydramnios complicated pregnancy, Ginekol Pol 2001; 72: 1107-11).

Catheters are used in the most varied areas of medicine. A balloon catheter is described in EP 1 557 193 B1, which is used to treat a congenital heart disease such as tricuspid atresia, pure pulmonary atresia or a complete reversal of large vessels. A balloon catheter is described in U.S. Pat. No. 5,226,889 A, which consists of a flexible shaft and at least one pair of inflatable balloons, the proximally situated balloon carrying a vessel support (stent). The vessel support is to be implanted into a patient by means of the balloon catheter. The above-mentioned catheters would not be suitable for use in an amnioinfusion. One problem is that the catheters cannot be fixed in the uterus wall. Furthermore, the problem of loss of fluid exists in amnioinfusion owing to the non-sealed puncture point in the uterus wall, so a continuous supply of fluid is necessary during the amnioinfusion. The danger of peritonitis is reduced or prevented by sealing using the balloon catheter system according to the invention.

A double balloon catheter for treating PPROM consists of a silicone tube with two separate balloons close to the cervical tip and a hole between these balloons, so an antiseptic solution, which is introduced from the outer end, can flow through the walls and branched channels into each balloon (Gramellini D, Fieni S, Kaihura C, Faiola S, Vadora E., Transabdominal antepartum amnioinfusion, Int J Gynaecol Obstet 2003; 83: 171-8). The described catheter is introduced via the cervix and the balloons are filled by infusion with PVP iodine solution through the branched channels. The balloons fix the catheter in the cervical channel, which is partly closed by operation clamps between the two balloons and is tightened after the filling thereof. The catheter described therein is to prevent the outflow of amniotic fluid via the cervix. However, when using this method there is a risk of an amnion infection syndrome (AIS) owing to infected amniotic fluid and extraneous bodies (catheters) in the cervix, as no continuous amnioinfusion takes place with fresh saline solution.

SUMMARY OF THE INVENTION

It is therefore an object of the present invention to provide a balloon catheter, which, on the one hand, can be securely and atraumatically fixed to the puncture point and, on the other hand, seals the puncture channel of the opening in a fluid-tight manner.

This object is achieved by a balloon catheter system for sealing puncture points or openings in body cavities, hollow organs or in percutaneous drainage operations in mammals with the features of claim 1. Preferred embodiments are to be found in the sub-claims.

The balloon catheter system according to the invention is suitable in general for sealing puncture points or openings in body cavities, hollow organs or in percutaneous drainage operations in mammals. The balloon catheter system consists of a filling catheter shaft or a filling channel for receiving a filling medium. At the distal end of the filling catheter shaft is a first balloon which can be filled with the filling medium. The balloon catheter system further contains a second, proximal balloon which can be filled with the filling medium and is spaced apart from the first distal balloon. The two balloons close the puncture point or the opening by being placed on both sides of the puncture point or opening when inflated. Arranged in the lumen of the filling catheter shaft is a guidable hollow needle. The guidable hollow needle is open at the shaft or shaft end and sized and arranged for filling the two balloons with the filling medium. The two balloons surround the shaft of the filling catheter. The filling catheter has a respective opening arranged in the balloon lumen to fill the two balloons, whereby when the hollow needle is drawn back, the distal balloon is filled with the filling medium first, followed by the filling of the second balloon.

The two balloons press against the walls of the body cavity or of the hollow organ so the puncture point or the opening is closed when the balloons are filled. The balloon catheter system can be introduced into the body cavity (for example the uterus during amnioinfusion) under sonographic control by means of a hollow needle (for example 18 G needle). Apart from the filling catheter, the balloon catheter system comprises an infusion channel or infusion catheter for the infusion with drainage of fluid into or out of body cavities, hollow organs or in percutaneous passages in mammals. In a preferred embodiment, arranged on the filling catheter is an infusion catheter, the distal end of which passes through the two balloons. For sealing, the shells of the two balloons enclose both the filling catheter and the infusion catheter. The filling catheter is used to fill the two balloons, while the infusion catheter can be used for the infusion of infusion fluids into the body cavity. As an alternative, the infusion channel is also suitable for draining fluids from organs or drainage operations. In one embodiment, the infusion catheter can be moved relative to the guide catheter through the balloons.

In a particular embodiment, the filling catheter and the infusion catheter are present in one component, i.e. the component has a channel for filling the balloon and a further infusion channel for the fluid supply or drainage.

Using the hollow needle which can be guided through the filling catheter, the balloon at the distal end of the filling catheter is filled with the filling medium (for example physiological saline solution) first. The filling process for the proximal balloon takes place by drawing back the hollow needle, so the proximally situated balloon can be filled via the opening present in the guide catheter. So the two balloons remain inflated, the filling catheter is constantly filled with filling medium and is therefore under pressure. Alternatively, check valves may also be provided in the filling channel. These may be located either at the foot end of the balloon or directly in the filling catheter. Alternatively, the check valves may also be arranged on the adapter or the filling device. These valves prevent the filling medium from flowing back owing to the balloon pressure.

The two balloons are preferably filled by means of a port system or other subcutaneous filling device, which is connected to the proximal end of the filling catheter and/or the hollow needle. The port system is implanted under the skin of the patient. It can be used to fill the balloon by means of a membrane. A further port system may be subcutaneously implanted for the infusion of physiological saline solution or for drainage by means of the infusion catheter. The port system thereby allows controlled refilling of the two balloons and the infusion or drainage of fluid into or out of the body through the infusion catheter or infusion channel. The port system is preferably a double port for the filling catheter and the infusion catheter. The hollow needle is preferably connected to an adapter for the port system or the subcutaneous filling device Once the two balloons have been inflated, the guide catheter is drawn back to the skin and expediently clamped off with a soft clamp by the operator to avoid the balloon collapsing and the catheter thereby being dislocated.

If the filling catheter and the infusion catheter are not configured in one component, it may be expedient for a guide wire which can be drawn out of the catheter to be additionally arranged in the lumen of the infusion catheter. As a result, the infusion catheter is stiffened and can be better guided to the puncture point of the body cavity or the hollow organ.

The type of filling medium depends on the respective purpose of use of the balloon catheter system according to the invention. The filling medium is physiological saline solution to treat a preterm premature rupture of the membranes (PPROM) by amnioinfusion. Continuous amnioinfusions can be carried out by means of the infusion catheter or the infusion channel, so the effect of the amnioinfusion is considerably increased during the treatment of PPROM. The filling medium may also be a contrast medium during use in patients.

In principal, the two balloons can also be simultaneously filled with the filling medium via the corresponding openings mentioned in the filling catheter. However, a serial filling is to be preferred to fix the catheter under sonographic control. A further possibility for serial filling of the two balloons is for the two balloons to consist of shells having different inflation resistances. As a result, the balloon with the lower inflation resistance is firstly inflated. Only when the pressure is increased further is the balloon with the higher inflation resistance also filled.

Instead of a port system, the hollow needle and/or the filling catheter may also be connected to an adapter, which is preferably equipped with a check valve so no filling medium can escape from the balloon. In one variant, the check valve is located in the catheter itself or at the foot end of the balloon.

Depending on the purpose of use, it may be advantageous if the two balloons and/or the catheters consist of biodegradable material, so the components of the balloon catheter system automatically dissolve after a certain time. A further operative intervention is thereby avoided.

The balloon catheter system according to the invention can be used anywhere where puncture points or openings have to be closed or fluids have to be drained/supplied from or into organs or body cavities.

One area of use of the balloon catheter system according to the invention is in amnioinfusion for treating a preterm premature rupture of the membranes (PPROM), in particular before the 34$^{th}$ completed week of pregnancy. This purpose of use is described in more detail in the example below.

In addition, the balloon catheter system according to the invention can be used for the infusion or drainage of fluid into or out of body cavities, hollow organs or in percutaneous passages of (non-human) mammals. The present invention therefore also relates to the use of the balloon catheter system in the treatment of a gastrointestinal anastomosis. In the case of a bowel obstruction, the balloon catheter system can contribute to relief, whereby peritonitis is prevented. Furthermore, it is suitable for draining bile from the gallbladder (for example in a pancreatic carcinoma). A further area of use is the drainage of fluid in a pleural effusion or a pericardial effusion. The present invention may also be used with Perianal abscesses and transcutaneous or transrectal drainage.

The mode of operation of the balloon catheter system according to the invention is to be described in more detail by means of an example.

EXAMPLE

The balloon catheter system according to the invention is used together with a port system to treat a preterm premature rupture of the membranes (PPROM) before the completed 34th week of pregnancy. PPROM was previously treated by repetitive amnioinfusions. However, the introduced amniotic fluid (physiological saline solution) flows away very rapidly in the patient, so the effect of the amnioinfusion is only slight. The balloon catheter system, which consists of a filling catheter for the two balloons and a further infusion catheter, is introduced into the uterus by an 18 G needle under sonographic control. A port system is implanted under the skin of the patient. The distal balloon arranged at the end of the catheter is filled with physiological saline solution using a hollow needle guided in the guide catheter. The filling catheter together with the distal balloon is then drawn back to the uterus wall so the distal balloon seals the puncture point from inside. The hollow needle is drawn back in order to then fill the second balloon located proximally outside the uterus via the opening in the filling catheter. The opening of the uterus produced by the puncture is sealed on the two sides by the two balloons. The guide catheter can then be drawn back to the skin and clamped off with a soft clamp in order to avoid the balloon being deflated and therefore translocation of the catheter. The balloons optionally have to be refilled and this takes place by means of the filling catheter and the port system implanted under the skin. The filling level of the balloon can be checked by means of ultrasound. Physiological saline solution (NaCl solution) is introduced via the infusion catheter into the uterus for continuous amnioinfusion.

The filling of the two balloons brings about an atraumatic fixing of the catheter and seals the opening in the uterus between the two balloons. The danger of ascending peritonitis triggered in the abdominal cavity by infected amniotic fluid is sharply reduced thereby. The development of lung hyperplasia and therefore the risk of a neonatal death of the child in a preterm premature rupture of the membranes is reduced by the use of a continuous amnioinfusion. This allows an extension of the pregnancy by up to several months.

A further advantage of the balloon catheter system according to the invention is that the infusion catheter can be introduced by means of a relatively large hollow needle to the puncture point or opening. As a result, the risk of injury from pain during the implantation is considerably reduced for the patient. A further advantage compared to known systems and methods is that the balloon catheter system can be guided with relatively thin hollow needles. In order to facilitate the guidance of the infusion catheter, a guide wire extending in the lumen is used. The guide wire can easily be removed again once the placing of the catheter has been effected. By using biodegradable material, the latex of the balloon dissolves in a few months, thus clearly facilitating the removal of the prenatal catheter.

The previously used catheters regularly dislocate from the uterus in a preterm premature rupture of the membranes after about a week, which can be avoided by using the balloon catheter system according to the invention, as the catheter can be visibly fixed in the amniotic sac.

BRIEF DESCRIPTION OF THE DRAWINGS

The invention is described in more detail in the drawing below.

FIG. 1 shows an embodiment of a balloon catheter system according to the invention. A hollow needle 12 is arranged in the filling catheter 14. Two fillable balloons 20, 22 are located at the distal end of the filling catheter 14. The proximal end of the hollow needle 12 is connected to an adapter 10 for filling the two balloons 20, 22. The filling medium (for example physiological NaCl solution) is introduced into the balloon 20, 22 via the hollow needle 12 and the filling catheter 14 (after removal of the hollow needle 12). The two balloons 20, 22 surround the filling catheter 14 and have a respective opening 23.1, 23.2 arranged in the balloon lumen for filling.

The distal balloon 20 is firstly filled with the filling medium via the opening 23.2 of the filling catheter 14 using the hollow needle 12. The filling catheter 14 is drawn back together with the filled distal balloon 20 to the uterus wall. The hollow needle 12 is then drawn back through the filling catheter 14 to the proximally situated balloon 22 in such a way that said balloon can be filled with the filling medium via the opening 23.1. The balloons 20, 22 are filled under sonographic control. The two balloons 20, 22, when filled, seal a puncture point or opening. The hollow needle 12 is drawn out of the filling catheter 14 and the proximal end 9.1 of the filling catheter 14 is connected to a port system, adapter or other filling device. Provided for the infusion or drainage is a further channel, which is shown as an infusion catheter 16 in the embodiment shown. A guide wire 18, which can be drawn out again once the catheter has been placed, is guided in the infusion catheter for easier introduction. The proximal end 9.2 of the infusion catheter 16 is connected to a port system (for example double port together with the filling catheter 14). The distal end 17 of the infusion catheter 16 projects into the body lumen. Physiological saline solution is continuously let into the uterus via the infusion catheter 16 for amnioinfusion.

The two balloons 20, 22 are preferably filled under sonographic control.

The puncture point is sealed and the catheter system fixed. A dislocation of the catheter is avoided, and this is a decisive advantage compared to conventionally used catheters.

The invention claimed is:

1. A balloon catheter system for sealing puncture points or openings in body cavities, hollow organs or in percutaneous drainage operations in mammals, comprising:

a filling catheter shaft configured for receiving a fluid medium having a proximal end and a distal end, said distal end having a first balloon having a first balloon lumen configured to be filled with the filling medium and a second balloon having a second balloon lumen configured to be filled with the filling medium, said second balloon arranged proximally spaced apart from said first balloon, whereby when said first balloon and said second balloon are inflated they are configured to close a puncture point or an opening by sealing said puncture point or opening on two sides, a hollow needle open at the shaft or shaft end and slidably engaged with a lumen of said filling catheter shaft whereby said hollow needle can be guided in the lumen of the filling catheter shaft, said hollow needle having a length sufficient to align said hollow needle opening with at least an opening for receiving said filling medium positioned within said first balloon, and an infusion catheter having a shaft with a distal end, at least said distal end passing through said first balloon and said second balloon, said filling catheter shaft positioned along an outer surface of said infusion catheter shaft thereby forming two independent and parallel lumens, said infusion catheter shaft having a distal end extending past said distal end of said filling catheter shaft and through said first balloon wherein when in use, said distal end is configured to project into puncture points or openings in body cavities, hollow organs or in percutaneous drainage operations in mammals, thereby providing or removing a fluid to or from a location distal from said first distal balloon and said second proximal balloon, wherein said first balloon and said second balloon enclose the filling catheter shaft and said infusion catheter, said second balloon having an opening sized and shaped to receive said filling medium, whereby, when the hollow needle is drawn back, the first balloon is filled with the filling medium prior to filling the spaced apart second balloon.

2. The balloon catheter system according to claim 1, further including a guide wire positioned in a lumen of the infusion catheter.

3. The balloon catheter system according to claim 1, characterized in that the proximal end of the filling catheter, the hollow needle, or combinations thereof, are connected to a port system or another subcutaneous filling device.

4. The balloon catheter system according to claim 3, characterized in that the proximal end of the infusion catheter is connected to a port system or another subcutaneous filling device.

5. The balloon catheter system according to claim 1, characterized in that the hollow needle, the filling catheter, or a combination thereof, are connected to an adapter having a check valve.

6. The balloon catheter system according to claim 1, characterized in that the filling medium is physiological saline solution.

7. The balloon catheter system according to claim 1, characterized in that the two balloons consists of shells having different inflation resistances.

8. The balloon catheter system according to claim 1, characterized in that the two balloons, the filling catheter, the infusion catheter, or a combination thereof, consist of biodegradable material.

9. The balloon catheter system according to claim 1, characterized in that the filling catheter, or the infusion catheter, or a combination thereof, can be introduced by means of a relatively large hollow needle to the puncture point or opening.

10. Use of the balloon catheter system according to claim 1 for sealing puncture points or openings in body cavities, hollow organs or in percutaneous drainage operations in mammals comprising:
    introducing said balloon catheter system to a puncture point or opening in a body cavity, hollow organ, or a percutaneous passage in a mammal;
    placing said first balloon on one side of said puncture point or opening;
    arranging said hollow needle to a position to fill said first balloon with a filling fluid;
    filling said first balloon with said filling fluid;
    placing said second balloon on a side of said puncture point or opening that is different than the side where said first balloon is positioned; and
    filling said second balloon with said filling fluid.

11. The use according to claim 10 for the infusion or drainage of fluid into or out of body cavities, hollow organs or percutaneous passages in mammals further including the step of infusing or draining of a fluid into or out of said body cavities, hollow organs or percutaneous passages through said infusion catheter.

12. The use according to claim 10 wherein said balloon catheter system is used for treating a preterm premature rupture of the membranes (PPROM), a gastrointestinal anastomosis, a bowel obstruction (ileus), drainage of bile from the gallbladder, a pleural effusion, a pericardial effusion or a perianal abscess.

13. A method for filling a balloon catheter system comprising:
    providing a balloon catheter system comprising a filling catheter shaft configured for receiving a fluid medium having a proximal end and a distal end, said distal end having first distal balloon having a first balloon lumen configured to be filled with the filling medium and a second proximal balloon having a second balloon lumen configured to be filled with the filling medium, said second proximal balloon spaced apart from said first distal balloon, whereby when said first distal balloon and said second proximal balloon are inflated they are configured to close a puncture point or an opening by sealing said puncture point or opening on two sides;
    a hollow needle open at the shaft or the shaft end and slidably engaged with a lumen of said filling catheter shaft whereby said hollow needle can be guided in the lumen of the filling catheter, said hollow needle having a length sufficient to align with at least an opening for receiving said filling medium in said first distal balloon; and an infusion catheter having a shaft with a distal end, at least said distal end passing through said first distal balloon and said second proximal balloon, said filling catheter shaft positioned along an outer surface of said infusion catheter shaft thereby forming two independent and parallel lumens, said infusion catheter shaft having a distal end extending past said distal end of said filling catheter shaft and through said first balloon wherein when in use, said distal end is configured to project into puncture points or openings in body cavities, hollow organs or in percutaneous drainage operations in mammals, thereby providing or removing a fluid to or from a location distal from said first distal balloon and said second proximal balloon;
    wherein said first distal balloon and said second proximal balloon enclose the filling catheter shaft and the infusion catheter, said second proximal balloon having an opening sized and shaped to receive said filling material, whereby, when the hollow needle is drawn back, the first distal balloon is filled with the filling medium prior to filling the spaced apart second proximal balloon;
    placing said filling catheter shaft into a puncture point or opening whereby at least a portion of said filling catheter having said first distal balloon extends through said puncture point or opening;
    filling said first distal balloon with a filling medium using said hollow needle;
    drawing said filled first distal balloon and said filling catheter shaft back to said puncture point or opening;
    positioning said hollow needle to fill said second proximal balloon; and
    filling said second proximal balloon with said filling medium.

* * * * *